United States Patent [19]

Warriner

[11] Patent Number: Plant 6,011

[45] Date of Patent: Sep. 15, 1987

[54] ROSE PLANT JACLIP

[75] Inventor: William A. Warriner, Tustin, Calif.

[73] Assignee: Jackson & Perkins Company, Medford, Oreg.

[21] Appl. No.: 792,909

[22] Filed: Oct. 30, 1985

[51] Int. Cl.[4] ..... A01H 5/00

[52] U.S. Cl. ..... Plt./9

[58] Field of Search ..... Plt./9

*Primary Examiner*—James R. Feyrer

*Attorney, Agent, or Firm*—Manford R. Haxton

[57] ABSTRACT

A miniature rose variety having very dense and compact habit of growth, small glossy leaves, continuous production of attractive pink flower clusters which combine to produce a plant with outstanding landscape appeal.

1 Drawing Figure

This present invention relates to a new and distinct variety of rose plant of the miniature class which was originated by crossing an unnamed variety with the variety Watercolor, U.S. Plant Pat. No. 4,031.

The primary objective of this breeding was to produce a new rose variety of the miniature class whose growth habit, foliage and flowering characteristics would permit its use as a landscape plant. This objective was substantially achieved along with other desirable improvements as evidenced by the following unique combination of characteristics which are outstanding in the new variety and which distinguish it from its parents as well as from all other varieties of which I am aware:

1. Vigorous dense and compact growth habit;
2. Formation of large clusters of pink blossoms;
3. Continuous and heavy production of flower clusters;
4. Production of small, dark, leathery leaves;
5. Little or no fragrance; and
6. Flowers bearing 40–50 petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Watercolor, U.S. Plant Pat. No. 4,031.

Classification:

*Botanical.*—Rosa hybrid.

*Commercial.*—Miniature.

FLOWER

Observations made from specimens grown in a greenhouse at Irvine, Calif. in June.

Blooming habit: Continuous.

Bud:

*Size.*—½" when petals start to unfurl.

*Form.*—Short, blunt top, globular.

*Color.*—When sepals first divide, a clear pink Red Group 55B; when half blown, upper side of petals pale pink Red Group 56A to B; lower side of petals essentially the same color as the upper side.

*Sepals.*—Color: Green 138B with some bronzing due to the sun. Three appendaged sepals lightly appendaged. Two unappendaged sepals hairy edge.

*Receptacle.*—Color: Green 138B. Shape: Funnel. Size: Large, relative to flower size. Surface: Hairy.

*Peduncle.*—Length: Short. Surface: Glandular. Color: Medium green. Strength: Stiff, erect.

Open bloom:

*Size.*—Small. Average open size 1½".

*Borne.*—Clusters, rounded, irregular.

*Stems.*—Short, strong.

*Form.*—When first open, flat, crowded and sometimes quartered. Permanence: Retains its form to the end.

*Petalage.*—Number of petals under normal conditions: 40–50.

*Color.*—Center of flower: Upper side of petals Red Group 56A to B; reverse side of petals, Red Group 56A to B. Base of petals, Near White. Major color: Red Group 56A to B.

*Variegations.*—None.

*Discoloration.*—General tonality at end of third day: Slight fading to 56D.

*Fragrance.*—Slight.

Petals:

*Texture.*—Thin.

*Shape.*—Outer petals oval with inner petals nearly linear.

*Form.*—Flat.

*Arrangement.*—Imbricated, sometimes quartered. Petaloids in center.

*Persistence.*—Drop off cleanly.

*Lastingness.*—On the plant, fair.

Reproductive parts:

*Anthers.*—Few. Color: Yellow. Arrangement: Regular around styles, mixed with petaloids.

*Filaments.*—Color: Yellow.

*Pollen.*—Gold Yellow.

*Styles.*—Color: Reddish.

*Stigmas.*—Color: White.

PLANT

Form: Shrub.

Growth: Vigorous, dwarf, upright, branching, compact.

Foliage: Number of leaflets on normal mid-stem leaves: 5 with ocasional 7.

*Size.*—Small.

*Quantity.*—Abundant.

*Color.*—New foliage: Reddish-bronze turning to Green 137A. Old foliage: Dark Green 139A.

Leaflets:

*Shape.*—Oval pointed.

*Texture.*—Leathery.

*Edge.*—Serrated.

*Serration.*—Single, small.

*Petiole.*—Rachis: Color: Reddish. Underside: Rough, with prickles.

*Stipules.*—Long, serrated.

*Disease resistance.*—Susceptible to mildew, blackspot, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Long, hooked downward.

*Color when young.*—Red.

Small prickles:

*Quantity.*—On main stalks, None. On laterals, Many.

*Color.*—Brown.

I claim:

1. A new and distinct variety of rose plant of the miniature class, substantially as herein shown and described, characterized particularly as to novelty by the unique combination of its very dense and compact habit of growth, small glossy leaves, continuous production of attractive pink flower clusters which combine to produce a plant with outstanding landscape appeal.

* * * * *

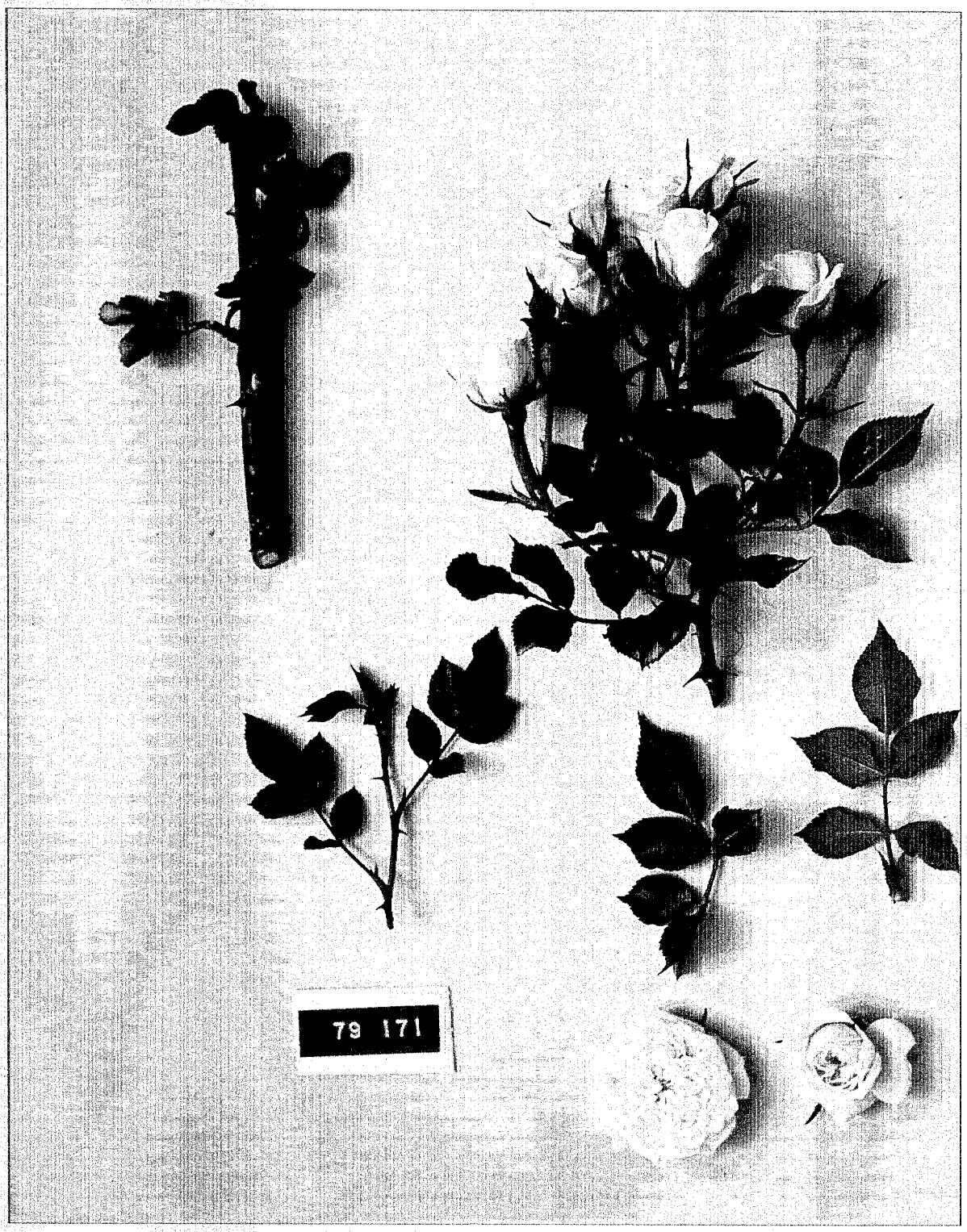
79 171